(12) United States Patent  
Heidner et al.

(10) Patent No.: US 7,785,340 B2
(45) Date of Patent: Aug. 31, 2010

(54) BONDING SLEEVE FOR MEDICAL DEVICE

(75) Inventors: Matthew C. Heidner, Maple Grove, MN (US); Thomas J. Holman, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1091 days.

(21) Appl. No.: 10/066,994

(22) Filed: Feb. 4, 2002

(65) Prior Publication Data

US 2003/0149465 A1 Aug. 7, 2003

(51) Int. Cl.
*A61M 29/00* (2006.01)
*A61F 2/06* (2006.01)

(52) U.S. Cl. .................. 606/194; 623/1.11; 606/108

(58) Field of Classification Search ............. 606/194, 606/108; 623/1.11; 604/103.01, 509, 524, 604/529

See application file for complete search history.

(56) References Cited

U.S. PATENT DOCUMENTS

| 4,194,509 | A | * | 3/1980 | Pickering et al. ............. 604/111 |
| 4,447,230 | A | * | 5/1984 | Gula et al. .................. 604/122 |
| 4,503,569 | A | | 3/1985 | Dotter ........................ 3/1.4 |
| 4,512,338 | A | | 4/1985 | Balko et al. .................. 128/1 |
| 4,732,152 | A | | 3/1988 | Wallsten et al. ............ 128/343 |
| 4,733,665 | A | | 3/1988 | Palmaz ...................... 128/343 |
| 4,848,343 | A | | 7/1989 | Wallsten et al. ............ 128/343 |
| 4,950,227 | A | | 8/1990 | Savin et al. .................... 604/8 |
| 5,019,090 | A | | 5/1991 | Pinchuk ..................... 606/194 |
| 5,044,726 | A | | 9/1991 | Grego ........................ 359/561 |
| 5,047,045 | A | | 9/1991 | Arney et al. ................ 606/194 |
| 5,108,416 | A | | 4/1992 | Ryan et al. ................. 606/194 |
| 5,156,594 | A | | 10/1992 | Keith ........................ 604/96 |
| 5,158,548 | A | | 10/1992 | Lau et al. .................... 604/96 |
| 5,234,456 | A | | 8/1993 | Silvestrini ................. 606/194 |
| 5,258,020 | A | | 11/1993 | Froix ......................... 623/1 |
| 5,267,959 | A | | 12/1993 | Forman ..................... 604/103 |
| 5,279,693 | A | | 1/1994 | Robinson et al. ......... 156/272.8 |
| 5,290,247 | A | * | 3/1994 | Crittenden ................. 604/171 |
| 5,403,341 | A | | 4/1995 | Solar ......................... 606/198 |
| 5,443,458 | A | | 8/1995 | Eury ........................ 604/891.1 |
| 5,443,907 | A | | 8/1995 | Slaikeu et al. ............... 428/375 |
| 5,453,090 | A | | 9/1995 | Martinez et al. .............. 604/53 |
| 5,501,759 | A | | 3/1996 | Forman ................... 156/272.8 |
| 5,534,007 | A | | 7/1996 | St. Germain et al. ........ 606/108 |
| 5,549,552 | A | | 8/1996 | Peters et al. ................. 604/96 |
| 5,569,184 | A | * | 10/1996 | Crocker et al. ............. 604/509 |

(Continued)

OTHER PUBLICATIONS

U.S. Appl. No. 09/684,255, filed Oct. 6, 2000, Justin Eric Plessel.

*Primary Examiner*—Vy Q Bui
(74) *Attorney, Agent, or Firm*—Vidas, Arrett & Steinkraus, P.A.

(57) ABSTRACT

A medical device delivery system comprises an inner tube, a medical device disposed about a portion of the distal region of the inner tube, a medical device sheath disposed about the medical device, a medical device sheath retraction device extending proximally from the medical device sheath and an outer sheath disposed about a portion of the medical device sheath retraction device. The distal end of the outer sheath terminates at least one medical device length proximal of the medical device. The medical device sheath is movable relative to the outer sheath and relative to the inner tube.

12 Claims, 5 Drawing Sheets

U.S. PATENT DOCUMENTS

| | | |
|---|---|---|
| 5,653,691 A | 8/1997 | Rupp et al. ................... 604/96 |
| 5,702,364 A | 12/1997 | Euteneuer et al. ............. 604/96 |
| 5,833,706 A | 11/1998 | St. Germain et al. ........ 606/194 |
| 5,897,537 A | 4/1999 | Berg et al. .................. 604/282 |
| 5,938,653 A | 8/1999 | Pepin .......................... 604/527 |
| 5,944,726 A | 8/1999 | Blaeser et al. ............... 606/108 |
| 5,957,930 A | 9/1999 | Vrba .......................... 606/108 |
| 5,968,069 A | 10/1999 | Dusbabek et al. ........... 606/194 |
| 5,980,530 A | 11/1999 | Willare et al. ............... 606/108 |
| 5,980,533 A | 11/1999 | Holman ...................... 606/108 |
| 6,007,543 A | 12/1999 | Ellis et al. ................... 606/108 |
| 6,017,577 A | 1/2000 | Hostettler et al. .......... 427/2.12 |
| 6,024,752 A | 2/2000 | Horn et al. ................... 606/192 |
| 6,036,697 A | 3/2000 | DiCaprio .................... 606/108 |
| 6,068,630 A | 5/2000 | Zucherman et al. ........... 606/61 |
| 6,068,634 A | 5/2000 | Lorentzen Cornelius et al. . 606/108 |
| 6,096,056 A | 8/2000 | Brown ........................ 606/194 |
| 6,139,525 A | 10/2000 | Davis-Lemessy et al. ... 604/103 |
| 6,176,849 B1 | 1/2001 | Yang et al. .................. 604/265 |
| 6,221,097 B1 | 4/2001 | Wang et al. ................. 623/1.11 |
| 6,221,467 B1 | 4/2001 | Nazarova et al. ............. 428/213 |
| 6,240,231 B1 * | 5/2001 | Ferrera et al. ............... 385/115 |
| 6,837,897 B2 * | 1/2005 | Holman et al. .............. 606/194 |

* cited by examiner

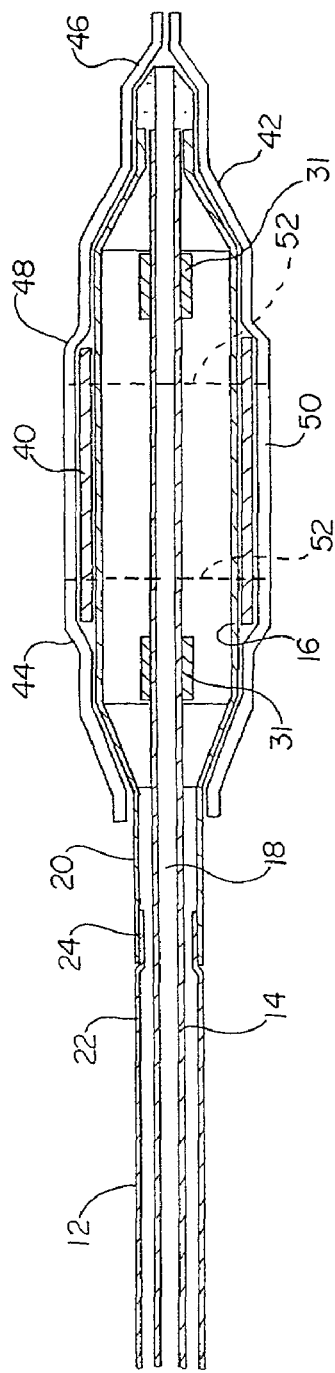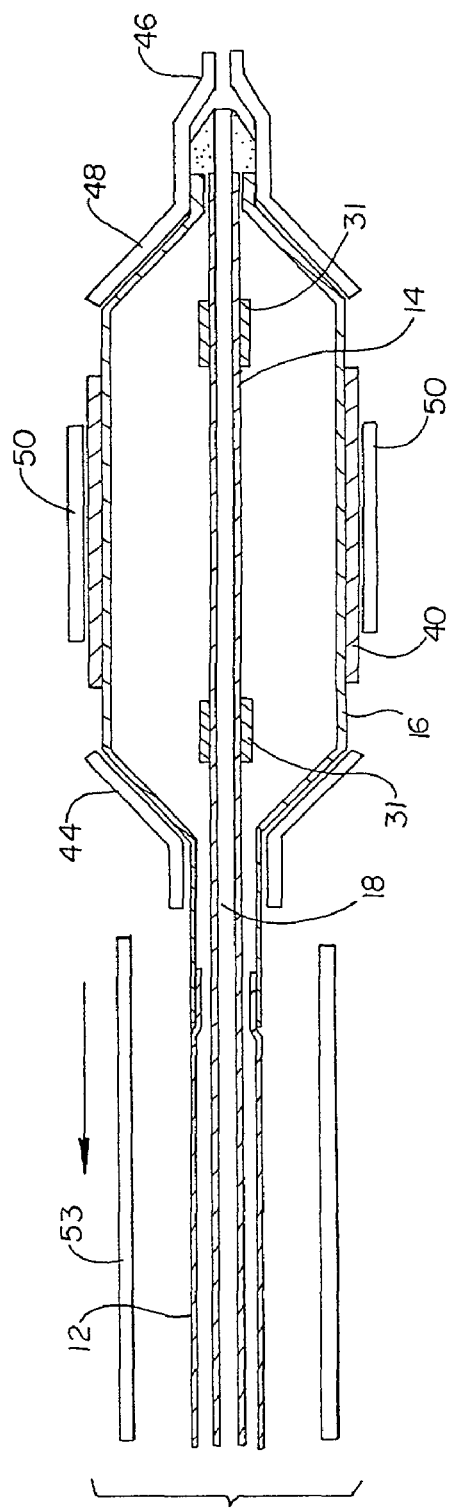

BONDING SLEEVE FOR MEDICAL DEVICE

FIELD OF THE INTENTION

This invention relates to catheters used for multiple procedures, including for delivering medical devices, such as stents, and a method of making the catheter systems. The delivery system employs a sleeve which aids in the bonding of parts of the catheter and is capable of becoming a part of the final system product.

BACKGROUND OF THE INVENTION

Catheters are used for many medical purposes. The present invention is not limited to a specific type of catheter, rather a method of making the catheter and the resulting product. Examples of catheters and procedures are addressed below for the sake of background.

In typical PTA or PTCA procedures, a guiding catheter is percutaneously introduced into the cardiovascular system of a patient and advanced through the aorta until the distal end is in the desired (coronary) artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter may have a guide wire lumen which is as long as the catheter or it may be a rapid exchange catheter wherein the guide wire lumen is substantially shorter than the catheter. Alternatively, a fixed wire balloon may be used. This device features a guide wire which is affixed to the catheter and cannot be removed.

To help prevent arterial closure, repair dissection, or prevent restenosis, a physician can implant an intravascular prosthesis, or a stent, for maintaining vascular patency inside an artery or other vessel at the lesion.

Stents are also used for a variety of other purposes including maintaining the patency of any physiological conduit including arteries, veins, vessels, the biliary tree, the urinary tract, the alimentary tract, the tracheobronchial tree, the genitourinary system, and the cerebral aqueduct.

The stent may either be self-expanding or balloon expandable. For the latter type, the stent is often delivered on a balloon and the balloon is used to expand the stent. The self-expanding stents may be made of shape memory materials such as nitinol or constructed of regular metals but of a design which exhibits self expansion characteristics.

The present invention is directed to the area of constructing catheters and other medical devices such as described above. Each catheter has many parts which must be interconnected with high accuracy and precision. Typically parts are adhered or thermally bonded together. Using retaining sleeves as an example (examples of which may be found in U.S. Pat. No. 4,950,227, U.S. Pat. No. 6,221,097, U.S. Pat. No. 6,068,634, U.S. Pat. No. 5,980,530, U.S. Pat. No. 5,968,069 and U.S. Pat. No. 5,044,726), welding may be accomplished by heating the retaining sleeve or by applying laser radiation to the retaining sleeve at a wavelength absorbed by the retaining sleeve. $CO_2$ lasers have proven to be particularly useful in this regard. Adhering and Welding methods are well known in the industry. An example of the use of laser welding may be found in U.S. application Ser. No. 09/684,255.

All U.S. patents and applications all other published documents mentioned anywhere in this application are incorporated herein by reference in their entirety.

Without limiting the scope of the invention in any way, the invention is briefly summarized in some of its aspects below.

SUMMARY OF THE INVENTION

The present invention is directed to using a sleeve to hold parts and joints of a catheter together such that they may be bonded together, wherein the sleeve remains on the catheter after the bonding to form parts of the final catheter product. With thermal bond welding, the sleeve is aligned and heat shrunk on the catheter to constrain the individual parts of the medical device, after which they are bonded in place. Instead of removing the sleeve, it remains to form part of the medical device. The sleeve which remains may form a useful part or a non-useful part which does not adversely affect the use of the medical device. As will be discussed below, the sleeve may vary in length along the catheter, providing for various final parts. In typical embodiments the sleeve, or at least a portion of the sleeve, is considered to be non-removable.

Initially, the sleeve is positioned over and around the catheter parts to be bonded together or to be encapsulated. A heating unit is used to apply heat to the sleeve to shrink it on the catheter. Heat, or any other method used to shrink the sleeve, is applied to one spot and then gradually moved along the length of the sleeve, gradually removing air and space between the sleeve and the catheter parts. The parts of a catheter then are bonded together via known techniques, such as adhesion, thermal welding, RF welding and ultrasonic welding. Portions, or all, of the sleeve are welded onto the catheter as well. After the bonding is complete the sleeve of the present invention remains in place providing an additional part, such as stent retaining sleeves, a distal tip or a protective cover. This eliminates the step of removing the holding sleeve in the normal process, saving time and finances.

The invention also contemplates certain coatings, pastes, gels or films may also be employed to constrain and/or form parts during bonding and become a part of the finished bonded component.

The invention is not limited to catheters. It may be applied to other medical items which use sleeves of the like to hold parts of the medical items together in order to bond them. Catheters are only used in the description for examples purposes.

The disclosure below involves simplifying the process of bonding construction as well as providing new methods of forming required parts of medical devices.

BRIEF DESCRIPTION OF THE FIGURES

FIG. 3 is a cross-sectional view of the distal end of a catheter illustrating a further embodiment of the invention;

FIG. 4 is a cross-sectional view of the embodiment shown in FIG. 3, having the balloon in expanded form;

DETAILED DESCRIPTION OF THE INVENTION

Figure 1:
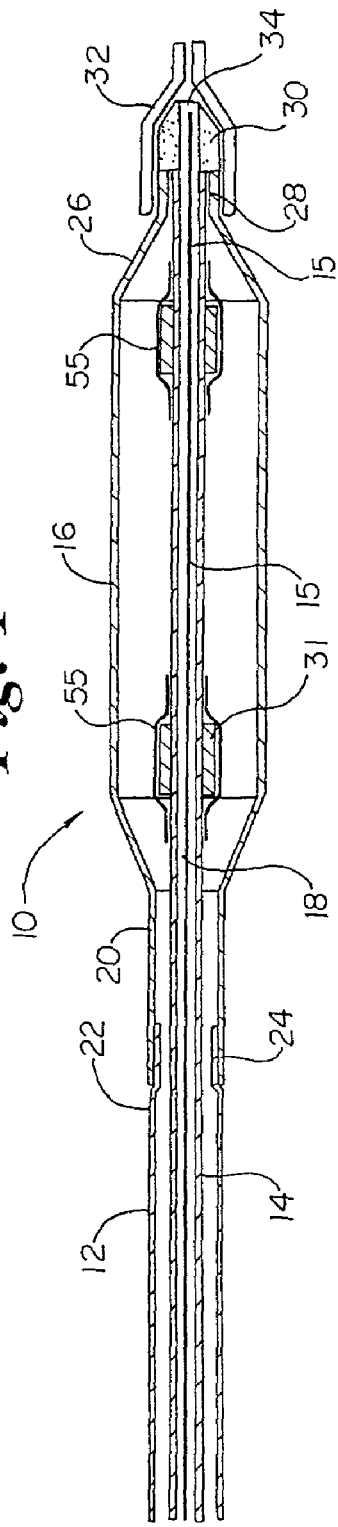
FIG. 1 is a cross-sectional view of the distal end of a catheter illustrating a particular embodiment of the invention.

While this invention may be embodied in many different forms, there are shown in the drawings and described in detail herein specific embodiments of the invention. The present disclosure is an exemplification of the principles of the invention and is not intended to limit the invention to the particular embodiments illustrated.

For the purposes of this disclosure, the term stent refers to stents, stent-grafts, grafts and other endoluminal prostheses whether self-expanding, balloon expandable, self-expanding and balloon expandable or otherwise expandable as are known in the art.

In addition to the over-the-wire embodiments (example also found in U.S. Pat. No. 5,980,533) shown in the figures, the inventive catheter system and methods may also be provided in any catheter system, such as plain balloon angioplasty catheters and rapid-exchange configurations. Examples of rapid-exchange catheters may be found in U.S. Pat. No. 5,534,007 and U.S. Pat. No. 5,833,706. The inventive stent delivery systems may also be made in fixed wire form. Examples of fixed-wire catheters may be found in U.S. Pat. No. 5,702,364.

The system may be adapted for use with a medical device such as a stent, for example, a self-expanding, balloon expandable or combination self-expanding and balloon expandable stent. The system may also be used for delivery of other medical devices for use in the body as well including, but not limited to, ultrasonic devices, laser devices, vena cava filters, drug coated sleeves and other implantable drug delivery devices and the like.

The inventive medical systems disclosed herein may also be provided with any of the features disclosed in U.S. Pat. No. 6,096,056, U.S. Pat. No. 6,068,634, U.S. Pat. No. 6,036,697, U.S. Pat. No. 6,007,543, U.S. Pat. No. 5,968,069, U.S. Pat. No. 5,957,930, U.S. Pat. No. 5,944,726, U.S. Pat. No. 5,653,691 and U.S. Pat. No. 5,534,007.

The stent delivery system may also comprise various coatings as are known in the art, including lubricious coatings to facilitate movement of the various parts of the system, as well as collagen-type coatings. More information concerning suitable coatings may be found in U.S. Pat. No. 5,443,907, and U.S. application Ser. Nos. 08/382,478, 09/306,939 and 09/316,502.

The invention is also directed to medical device delivery systems and catheters produced using the inventive methods.

For the purposes of the detailed description of the invention, figures of a portion of the distal end of a typical balloon catheter will be used. It should be understood, as mentioned above, that the present invention is applicable to other portions of the catheter as well as other medical devices, which use a constraining sleeve for bonding parts and joints together. It should also be understood that the materials used may be any of those materials known in the art where applicable.

For the purposes of this disclosure, unless otherwise indicated, identical reference numerals used in different figures refer to the same component.

FIG. 1 illustrates the distal end of a typical balloon catheter 10 for delivering stent to a specific location within the body. The catheter 10 has an outer sheath 12 which extends over the body of the catheter 10. The catheter also comprises an inner shaft 14 forming an inner lumen 18, which allows access for a guide wire 15. A balloon 16 is mounted on the catheter 10 at the distal end. The proximal end of the balloon 20, in this type of catheter, is bonded to the distal end 22 of the outer sheath 12 at point 24. In other embodiments, the proximal end of the balloon may also be bonded to the inner shaft. The catheter is typically guided through a guide catheter 53 (shown in FIG. 4).

The distal end of the balloon 26 is mounted on the inner shaft 14 and will eventually be bonded to the inner shaft 14 at point 28. There is a distal tip 30 at the distal end of the catheter, but, as will be explained later, it may not be needed due to the forming of a distal tip by the sleeve 32 (hereafter called sleeve 32). Marker bands 31 are also illustrated.

The sleeves of the present embodiments suitably comprise non-cross linked thermoplastics, such as olefins and tecothanes, so that bonding and flowing is enhanced.

Figure 5:
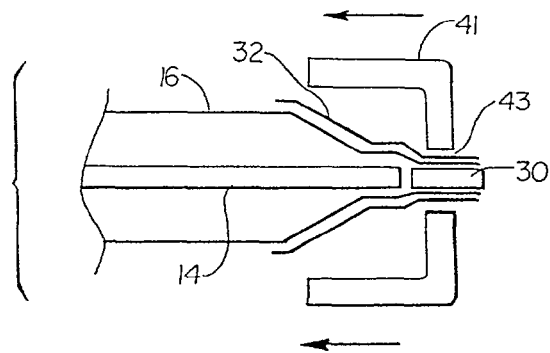
FIG. 5 is a cross-section view of the embodiment of FIG. 1, wherein the sleeve is being heat shrunk onto the catheter.

The parts of the catheter to be made are held together via the sleeve 32. As mentioned above, the sleeve 32 is heat shrunk around the parts to be permanently bonded to constrain them in place as a bonding aid. This is done typically at 200-250° F., however, the material dictates the temperature. In this instance, as shown in FIG. 5, a heating element 41, such as a heat gun, a hot block or hot jaws, is used to apply heat to a point 43 on sleeve 32. The heating element can be applied directly on the surface of the sleeve 32. The heating element 41 can be then moved along the length of the sleeve 32, as shown, causing the sleeve 32 material to shrink, and optionally flow. Depending on the type of heating element used, movement may not be needed. The temperature is dictated by the material used. The heat must be sufficient to shrink the sleeve, but not so hot as to break the material down so as to destroy the integrity of the sleeve. By heating the material at or slightly above its melt temperature, the material will flow and create a fuse bond where bonds are desired.

This bonding may be dictated by the part which is being made. For example, in the case of forming a stent retaining sleeve, it may be desirable to only bond a part of the sleeve, leaving the remaining portion shrunk but not bonded. This allows the stent retaining sleeve to be capable of moving relative to the balloon for effective release of the stent during delivery. Complete bonding of the parts together at desired spots can be completed during the welding procedures.

The moving heating element seals the sleeve 32 to the catheter, holding the parts of the catheter together. The longitudinal moving of the heating element and the flow of the sleeve 32 material stretches the material out and removes any air pockets to result in a tight, uniform fit. The shrinking of the sleeve 32 can start at one end of the sleeve 32, proceeding to the opposite end. However, it is contemplated that the shrink may start at any place along the sleeve, gradually moving longitudinally.

The bonding of the parts of the catheter is then started, suitably done by laser welding. The sleeve remains as part of the final product and in some cases can be used to hold a loaded stent in place during sterilization. In FIG. 1, sleeve 32 remains to form the distal tip of the catheter. In all cases, the sleeve may also act as an added protective layer and be lubricated for easy movement through body lumens.

The port 34 of the inner lumen 18 may be closed due to the heat shrunk sleeve 32 until needed. If the catheter were a back loaded catheter, as shown, the guide wire 15 would pierce the closed port when needed.

A sleeve 55 may also be used to secure the marker bands 31 to the inner shaft 14 during the securement of the marker bands 31 to the shaft 14. Sleeve 55 remains a part of the catheter and may be a soft protective cover over the marker band 31 to protect the balloon 16 from being damaged by the marker bands 31. Sleeve 5 may be used in any of the embodiments.

Figure 2:
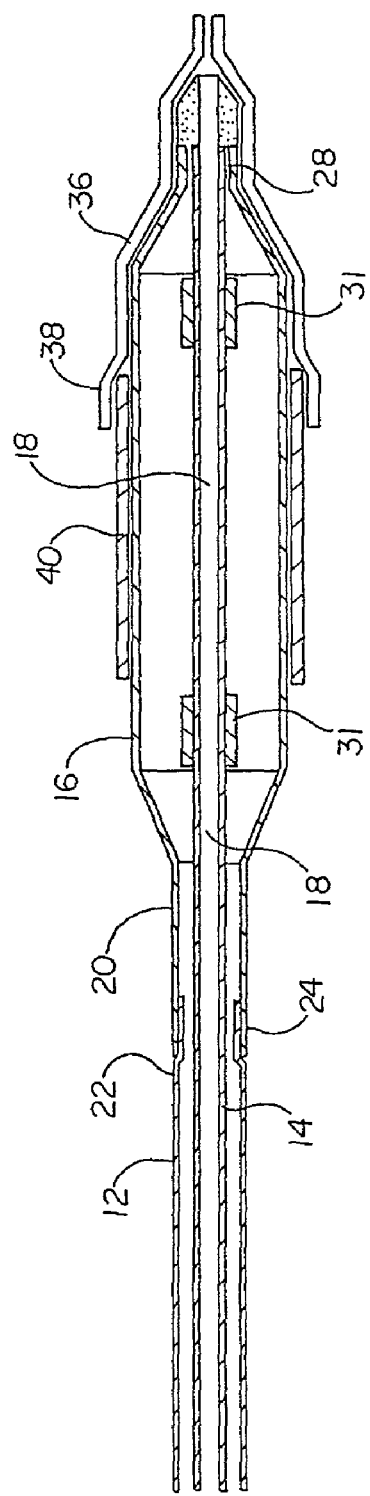
FIG. 2 is a cross-sectional view of the distal end of a catheter illustrating a further embodiment of the invention.

In the embodiment shown in FIG. 2, a larger sleeve 36 is used. The word larger is used in terms of length of coverage over the catheter. In addition to the functions of sleeve 32, as described above, sleeve 36 also forms a distal stent retaining sleeve 38. As mentioned above, stent retaining sleeves are known. The materials and methods for applying and using the sleeve 32 are similarly applicable here. Retaining sleeve 38 can aid in holding the stent 40 in place.

The invention also contemplates a sleeve which may extend up the cones of the balloon, but not over the end of the stent. Such a sleeve may aid in balloon rewrap as well as provide leading lubrication for the catheter to aid in trackability of the stent.

The use of retaining sleeves to retain a stent on a catheter has been disclosed in a number of patents including U.S. Pat. No. 4,950,227 to Savin et al., U.S. Pat. No. 5,403,341 to Solar and U.S. Pat. No. 5,108,416 to Ryan et al., as well as U.S. Pat. No. 5,944,726 and U.S. Pat. No. 5,968,069. One or more retaining sleeves typically retain the stent on the catheter when the stent is in an unexpanded state. Upon expansion of the stent, the retaining sleeves release the stent.

FIG. 3 illustrates another embodiment. The method of applying the stent is the same. In this embodiment, an even larger sleeve 42 is used. In addition to the function of sleeves 32 and 36, as described above, sleeve 42 also forms a proximal stent retaining sleeve 44 which extend down the proximal end of the balloon 16, over the balloon waist 20. It should be understood that, the sleeve 42 may extend further in the proximal direction to provide for bonding at point 24. In this embodiment, sleeve 42 covers the entire balloon section, as well as the stent 40.

As described above, sleeve 42 constrains the parts of the catheter in this area until they are fully bonded, such as through laser welding. As with the other sleeves, sleeve 42 remains in place for sterilization and use. As part of the final catheter, sleeve 42 forms a distal tip 46, a distal stent retaining sleeve 48 and a proximal stent retaining sleeve 44. Sleeve 42 also forms a tubular member 50 which surrounds the stent. This member may be used in the final product or discarded, according to the application. To allow the stent to eventually be separated from the catheter the stent retaining sleeves 44, 48 are separated from the tubular member 50 by tear away perforations 52. The tubular member 50 also may be drug eluting. It should be understood that an embodiment may comprise a catheter wherein the heat shrinkable sleeve covers the stent, but only provides one stent retaining portion, and therefore only one circumferential perforation.

FIG. 4 shows the embodiment of FIG. 3 wherein the guide catheter 53 is withdrawn and the balloon 16 is expanded. As can be seen, the retaining sleeves 44, 48 tear away, or are peeled, from the tubular member 50 and fall away from the stent 40. The tubular member 50 must be made from a material which can expand with the stent.

If the tubular member 50 is meant to be left in the body, it preferably should be biocompatible. In such a case, the stent effectively pushes it into the artery wall. Biocompatible materials are well known in the art. They include, but are not limited to TEFLON and urethanes. The material may further include pharmaceutical agents to prevent restenosis. Such agents may comprise proteins with small molecules, such as taxol-containing drugs, nucleotides and actinomycine. Materials which eventually dissolves or disintegrates may also be used, such as polylactic acid. The tubular material 50 may also incorporated drugs which aid in the healing and acceptance of the stent, such as anti-thrombogenic agents. These types of agents are well known.

Teflon or a flouropolymer may also be used for the tubular member 50 to protect against hyperplasia or restenosis. The member prevents the vessels from growing back in on the delivered stent.

The present invention contemplates a multi-material sleeve 42, which is preassembled. In such a sleeve, the retaining sleeve portions 44, 48 may be made of a material which has less elasticity than the tubular member. The sleeve 42 may vary in other characteristics as well, such as lubricity and strength.

Figure 6:
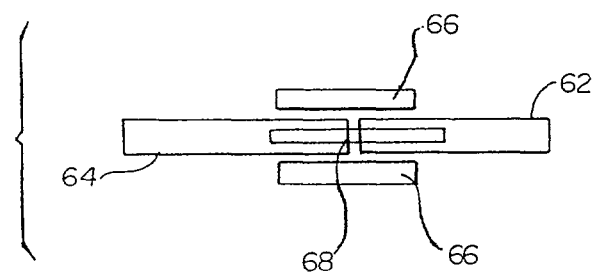
FIG. 6 is a cross-section view of a catheter mid-shaft to be bonded.

It should be understood that the invention contemplates the use of the sleeve in any welding application. FIG. 6 shows the process of a catheter midshaft bonding between a proximal shaft 64 and a distal shaft 62. Shaft 64 may be a metal hypotube. The ends of the shafts are fitted onto a mandrel 68 for support. In accordance with examples of the methods, a support mandrel may be used as support for other parts to be bonded together. A sleeve 66 is shrunk around the junction to be bonded. The sleeve 66 is then bonded to shafts 64, 62, providing a tight connection. The sleeve allows for a connection which does not require that the shafts overlap, as seen in FIG. 1 at 24, and thus a smooth inner transition. It should be understood that the connection at 24 may also be created by this method.

FIGS. 7-10 illustrate the use of a sleeve 84 in connecting and sealing between a mid-shaft 72, a distal shaft 74 and a distal inner shaft 76, which functions as a guide wire lumen, in a rapid exchange catheter. Rapid exchange catheters are well known in the art. These catheters are generally characterized in that a port 78 allows for insertion of certain parts from the outside of the catheter to the inside anywhere along the length of the catheter. In typical rapid exchange catheters, the port is for insertion of a guide wire or an inflation lumen. Only the portion showing the port 78 and connection between the mid-shaft 72, distal shaft 74 and distal inner shaft 76 is shown.

Figure 7:
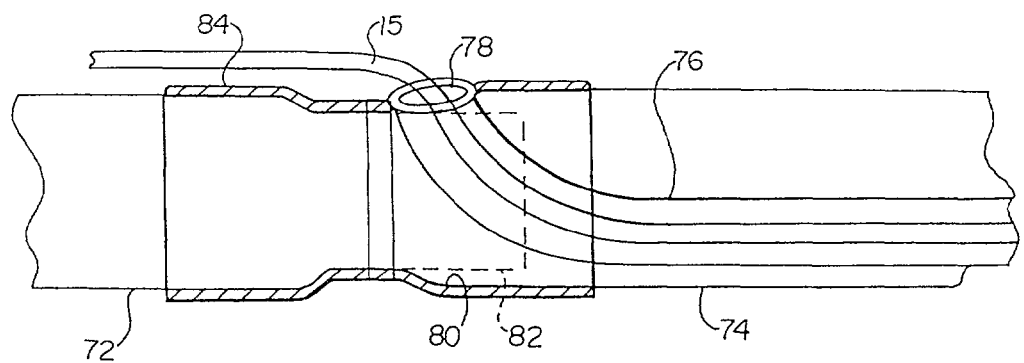
FIG. 7 is a cross-section view of a portion of a rapid exchange catheter illustrating a further embodiment.

FIG. 7 shows the distal end 82 of the mid-shaft 72 inserted into the proximal end 80 of the distal shaft 74. It should be understood that the distal shaft 74 could be inserted into the midshaft 72 in an inverted manner. A port 78 is positioned in the wall of the distal shaft 74 and/or the wall of the midshaft, depending on the port's positioning. In this particular embodiment, the port 78 opens into a guide wire lumen 76, which is bonded to the distal shaft 74 and extends distally to the end of the catheter. A sleeve 84 is shrunk around the juncture of the shafts 72, 74. The shafts are then bonded together.

Figure 8:
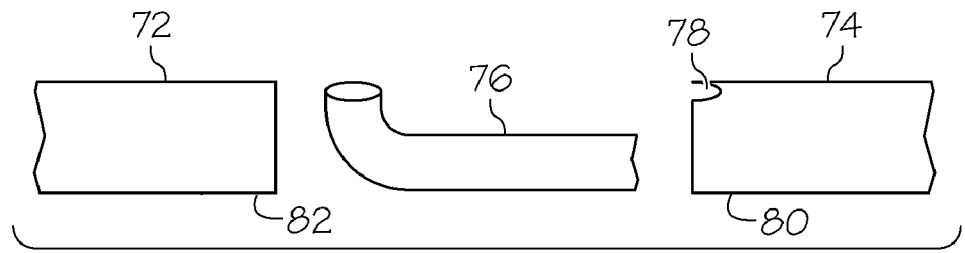
FIG. 8 is an exploded cross-section view of a portion of a rapid exchange catheter illustrating a further embodiment.
Figure 9:
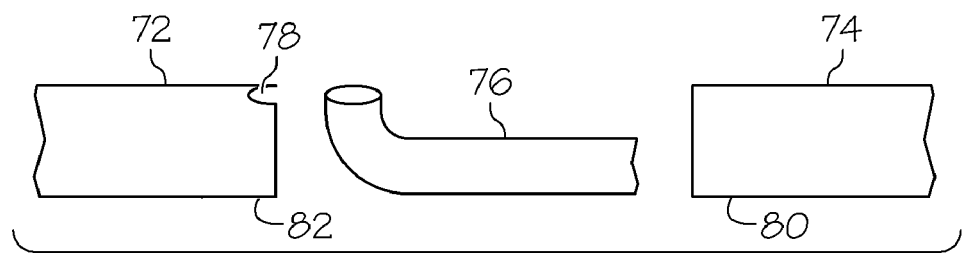
FIG. 9 is an exploded cross-section view of a portion of a rapid exchange catheter illustrating a further embodiment.
Figure 10:
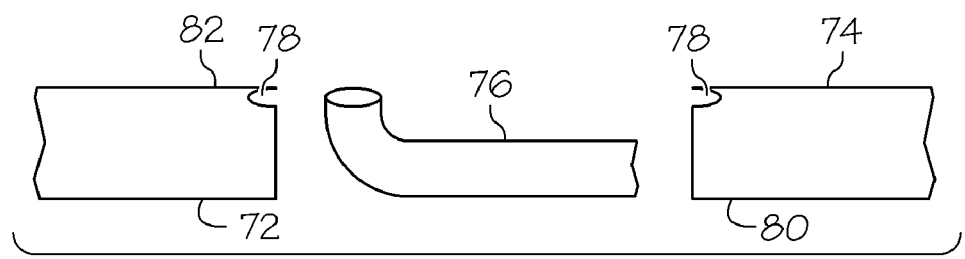
FIG. 10 is an exploded cross-section view of a portion of a rapid exchange catheter illustrating a further embodiment.

The sleeve 84 also allows for a connection between the shafts 72, 74 with a smooth internal transition, as shown in FIGS. 8-10. In these embodiments, as with the embodiment shown in FIG. 6, the ends 82, 80 of the shafts 72, 74 are adjacent, but not overlapping. The shrunken sleeve 84 is used to connect the shafts 72, 74. The shafts 72, 74 need not be bonded directly to each other. Instead, the sleeve 84 may be bonded to each shaft.

FIGS. 8-10 also show various positions of the port 78. FIG. 8 shows the port 78 in the proximal end 80 of the distal shaft 74, FIG. 9 shows the port 78 in the distal end of the midshaft and FIG. 10 shows the port 78 being formed in the ends 80, 82 of both shafts 74, 72.

Figure 11:
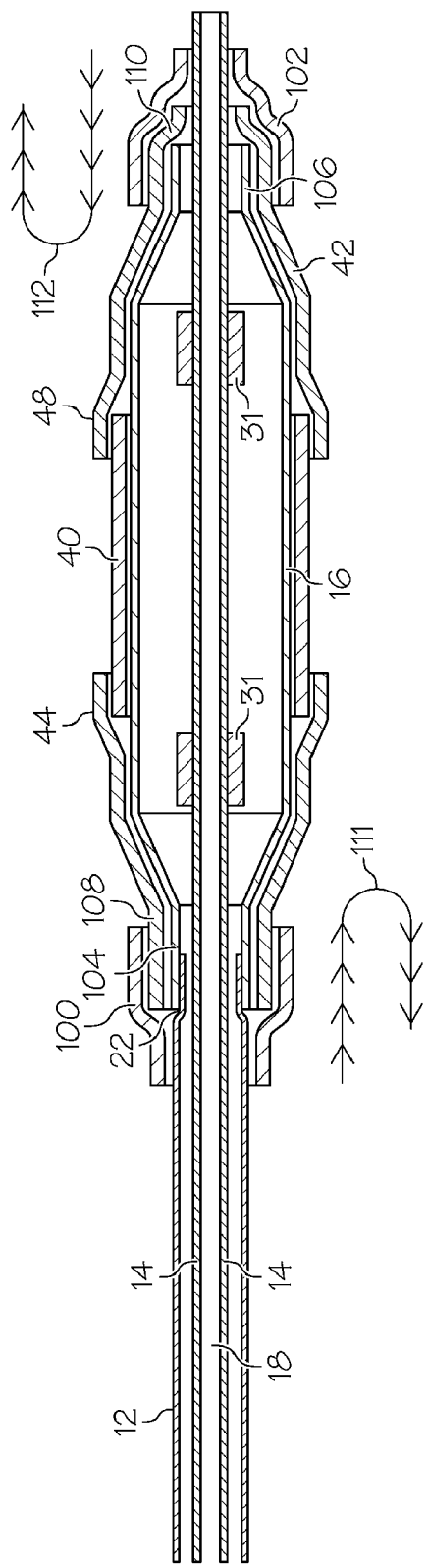
FIG. 11 is a cross-sectional view of the distal end of a catheter illustrating a further embodiment of the invention.

FIG. 11 illustrates a further embodiment of the invention. This particular embodiment comprises a balloon 16 attached to the catheter, a proximal stent retaining sleeve 44 and a distal stent retaining sleeve 42, an outer sheath 12, a stent 40 and a proximal shrunken sleeve 100 and a distal shrunken sleeve 102.

The invention contemplates incorporating the proximal sleeve 100 or the distal sleeve 102 or both. As can be seen, the balloon is positioned on the catheter and then the stent retaining sleeves 108, 110 are positioned. The stent retaining sleeves may extend beyond the ends of the balloon, as shown with sleeve 110, to the ends of the balloon, as shown with sleeve 108, or they may stop short of the ends of the balloons. It should be understood that the ends of the balloon 104 and the outer sheath 22 may overlap in either manner. Only the manner in which the balloon end overlaps the sheath end is shown.

In this particular embodiment, the shrunken sleeves 100, 102 are shrunk down over these junctures. The bonds are then welded into place and the sleeves 100, 102 are left in place. Arrows 111, 112 illustrate the preferred direction in which the sleeves 100, 102 are welded.

Figure 12:
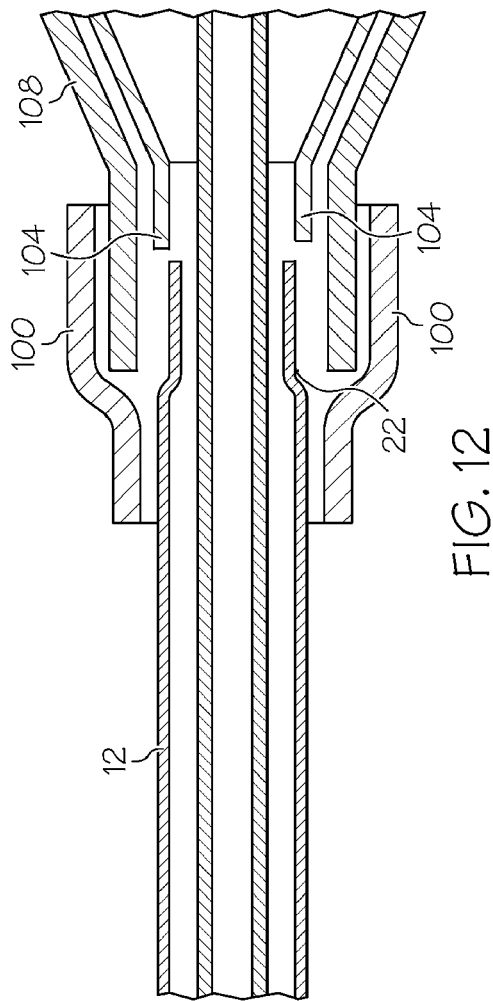
FIG. 12 is a cross-sectional view of the distal end of a catheter illustrating a further embodiment of the invention.

FIG. 12 illustrates an alternative juncture configuration between the stent retaining sleeve, the balloon and the outer sheath. In this particular configuration, end of the balloon 104 does not overlap the end 22 of the outer sheath 12. The stent retaining sleeve 108 extends beyond the end of the balloon and over or under the end of the outer sheath. The shrunken sleeve 100 is then shrunk down over the juncture and the components are then welded, as discussed above.

For the examples shown, the medical balloon may be made of any suitable material including Pebax®. Other suitable materials are disclosed in U.S. Pat. No. 6,024,752, and U.S. Pat. No. 6,036,697.

For the examples shown, suitable materials for the outer sheath/shaft are well known in the art and include high density polyethylene (HDPE) and SURLYN® and those materials disclosed in U.S. Pat. No. 6,036,697 and U.S. Pat. No. 5,543,007.

The effectiveness of the bonding may be limited by the compatibility of the adjacent materials. Adjacent materials which provide covalent bonding or molecular entanglement are examples of suitable material.

For the examples shown, the inner shaft may be made of a flexible construction having any collapse strength. The inner shaft may also be made of an incompressible construction, such as a polymer encapsulated braid or coil. The flexibility of the braid/coil allows the medical device delivery system to navigate through body lumens and the incompressibility of the braid/coil aids in maintaining the integrity of the system and aids in deployment accuracy when during release of the medical device. The braid/coil may be comprised of stainless steel or nitinol, but desirably stainless steel encased in a polymer such as a polyimide, HDPE, Teflon or urethane, but desirably polyimide or Teflon. Other suitable materials which may be used are well known in the art.

Portions of the sleeves may be radio opaque for the user to track the positioning within the body. Methods of making the sleeve material radio opaque are well known. Suitable examples include doping the raw material with radio opaque materials.

The above sleeves also provide strain relief on joint of the catheter by diffusing the strain placed upon the catheter during storage and use.

Portions of the sleeves may be removed while other portions are maintained as part of the final catheter when desired.

The sleeve may also take the form of a film/coating, paste or gel. Typically, this embodiment may be used in parts of catheters which are not subject to a significant degree of contraction or pressure, such as a distal tip. A spray producing a dried film can be used, providing adequate axial resistance for welding purposes. Suitable materials include urethanes, polystyrenes and polyesters. For pastes or gels, suitable ground up micro particles are dissolved and applied to the medical device where needed. Axial resistance is provided with time drying or via a catalyst.

The medical device delivery systems may be subjected to additional processing steps prior to and/or subsequent to disposing the retaining sleeve about the stent and balloon. For example, bumpers and/or marker bands may be disposed about the inner tube or other portions of the medical device delivery system. A retractable sheath may be provided over the balloon and stent. A manifold may also be provided at the proximal end of the medical device delivery system. Other additional steps include providing to the inventive medical device delivery devices any of the features disclosed in U.S. Pat. No. 6,096,056, U.S. Pat. No. 6,007,543, U.S. Pat. No. 5,968,069, U.S. Pat. No. 5,957,930, U.S. Pat. No. 5,944,726 and U.S. Pat. No. 5,653,691.

In addition to being directed to the embodiments described above and claimed below, the present invention is further directed to embodiments having different combinations of the dependent features described above and/or claimed below.

Every patent, application or publication mentioned above is herein incorporated by reference.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each single dependent claim format which creates a dependency from a prior antecedent-possessing claim other than the specific claim listed in such dependent claim below (e.g. claim 6 may be taken as alternatively dependent from any of claims 2-5, claim 4 may be taken as alternatively dependent from claim 3; etc.).

What is claimed is:

1. A catheter comprising: a distal shaft having a length, a substantially constant outer diameter along a majority of its length, a lumen and a proximal end; a proximal shaft having a length, a substantially constant outer diameter along a majority of its length, a wall defining an inner lumen and a distal end, the distal end of the proximal shaft being connected to the proximal end of the distal shaft and the lumens of the respective shafts being in fluid communication with one another; a heat shrinkable sleeve having a longitudinal length extending from a proximal-most end to a distal-most end of said heat shrinkable sleeve, and overlapping the proximal end of the distal shaft and the distal end of the proximal shaft providing a water seal, wherein said longitudinal length consists of a small portion of the distal end of the proximal shaft and a small portion of the proximal end of the distal shaft; and a port, wherein the port is positioned between the first and second ends of the heat shrinkable sleeve and formed at least partially transversely through the wall of the proximal shaft, wherein the catheter is sterilized and prepared to safely enter a body.

2. The catheter of claim 1, wherein the distal shaft and the proximal shaft overlap.

3. The catheter of claim 1, wherein the heat shrinkable sleeve comprises a thermoplastic polymer which is substantially not cross-linked.

4. The catheter of claim 1, the heat shrinkable sleeve being gradually heat shrunk along its length around the distal shaft and proximal shaft.

5. The catheter of claim 1, wherein the retaining sleeve is formed from a material chosen from the group consisting of a liquid film, wherein the film solidifies prior to the bonding of the balloon to the shafts or a gel, wherein the gel hardens prior to the bonding of the balloon to the shafts.

6. The catheter of claim 1, wherein the proximal shaft is metal.

7. The catheter of claim 1, further comprising an inner shaft within the distal shaft, wherein the inner shaft is in communication with the port.

8. The catheter of claim 1, wherein the port is formed in the proximal shaft.

9. The catheter of claim 1, wherein the port is at least partially formed in the distal shaft.

10. The catheter of claim 1, wherein the port is formed in the distal shaft and the proximal shaft.

11. The catheter of claim 1, wherein the distal shaft and the proximal shaft abut each other.

12. The catheter of claim 7, wherein the inner shaft is a guide wire shaft, through which a guide wire may be used.

* * * * *